United States Patent [19]

Dearnaley et al.

[11] Patent Number: 5,605,714

[45] Date of Patent: *Feb. 25, 1997

[54] TREATMENTS TO REDUCE THROMBOGENETICITY IN HEART VALVES MADE FROM TITANIUM AND ITS ALLOYS

[75] Inventors: Geoffrey Dearnaley; James Lankford, Jr., both of San Antonio, Tex.

[73] Assignee: Southwest Research Institute, San Antonio, Tex.

[*] Notice: The term of this patent shall not extend beyond the expiration date of Pat. No. 5,593,719.

[21] Appl. No.: 472,495

[22] Filed: Jun. 7, 1995

Related U.S. Application Data

[63] Continuation-in-part of Ser. No. 220,234, Mar. 29, 1994.

[51] Int. Cl.$^6$ .............................. B05D 3/00; C23C 14/06; B01S 3/06; A61F 2/24
[52] U.S. Cl. ................. 427/2.24; 427/2.25; 427/525; 427/527; 427/530; 427/528; 623/2; 623/66; 423/446; 428/450
[58] Field of Search ................... 427/2.24, 2.26, 427/2.25, 527, 525, 530, 528, 534; 623/2, 12, 18, 19, 20, 21, 22, 23, 66; 428/450; 423/446

[56] References Cited

U.S. PATENT DOCUMENTS

| | | |
|---|---|---|
| 4,362,681 | 12/1982 | Spector et al. . |
| 4,410,611 | 10/1983 | MacIver . |
| 4,452,827 | 6/1984 | Kolev et al. . |
| 4,465,715 | 8/1984 | Manabe et al. . |
| 4,486,286 | 12/1984 | Lewin et al. . |
| 4,495,044 | 1/1985 | Banks . |
| 4,554,208 | 11/1985 | MacIver et al. . |
| 4,647,494 | 3/1987 | Meyerson et al. . |
| 4,698,236 | 10/1987 | Kellogg et al. . |
| 4,725,345 | 2/1988 | Sakamoto et al. . |
| 4,743,493 | 5/1988 | Sioshansi et al. . |
| 4,746,538 | 5/1988 | Mackowski . |
| 4,756,964 | 7/1988 | Kincaid et al. . |
| 4,772,513 | 9/1988 | Sakamoto et al. . |
| 4,778,469 | 10/1988 | Lin et al. . |
| 4,822,355 | 4/1989 | Bhu vaneshwar ............ 623/2 |
| 4,822,466 | 4/1989 | Rabalais et al. . |
| 4,842,937 | 6/1989 | Meyer et al. . |
| 4,877,677 | 10/1989 | Hirochi et al. . |
| 4,961,958 | 10/1990 | Desphandey et al. . |
| 4,981,071 | 1/1991 | Fnke ............................ 427/573 |
| 4,992,298 | 2/1991 | Deutchman et al. . |
| 5,009,923 | 4/1991 | Ogata et al. . |
| 5,028,451 | 7/1991 | Ito et al. . |
| 5,064,682 | 11/1991 | Kiyama et al. . |
| 5,084,151 | 1/1992 | Vallana et al. . |
| 5,130,161 | 7/1992 | Mansur et al. . |
| 5,133,757 | 7/1992 | Sioshansi et al. . |
| 5,133,845 | 7/1992 | Vallana et al. . |
| 5,135,808 | 8/1992 | Kimock et al. . |
| 5,169,597 | 12/1992 | Davidson et al. ............ 623/16 |
| 5,176,710 | 1/1993 | Hahn et al. . |
| 5,192,330 | 3/1993 | Chang et al. . |
| 5,192,523 | 3/1993 | Wu et al. . |
| 5,219,363 | 6/1993 | Crowninshield et al. . |
| 5,228,451 | 7/1993 | Bales et al. . |
| 5,252,174 | 10/1993 | Deguchi et al. ............ 427/527 |
| 5,270,252 | 12/1993 | Papanicolaou ............ 437/176 |
| 5,314,492 | 5/1994 | Hamilton et al. . |
| 5,391,407 | 2/1995 | Dearnaley ................ 427/528 |
| 5,415,704 | 5/1995 | Davidson ................. 623/16 |
| 5,425,777 | 6/1995 | Sarkisian et al. ............ 623/21 |

FOREIGN PATENT DOCUMENTS

| | | |
|---|---|---|
| 548799A | 6/1993 | European Pat. Off. . |
| 0548788A | 6/1993 | European Pat. Off. . |
| 62-196371 | 8/1987 | Japan . |
| 62-202897 | 9/1987 | Japan . |
| 1147067-A | 6/1989 | Japan . |

OTHER PUBLICATIONS

J. Lankford, et al. "Adherence of diamondlike carbon coatings on total joint substrate materials," *Nuclear Instruments and Method in Physics Research*, B80/81 (1993) 1441–1445. No Month.

John H. Dumbleton, "The Clinical Significance of Wear in Total Hip and Knee Prostheses," *Journal of Biomaterials Applications*, 3 (Jul. 1988) 3–32.

G. Dearnaley, et al. "Bioapplications of Diamond–Like Carbon Coatings," 4th World Biomaterials Congress (Apr. 1992) 9 pages.

C. J. Bedell, et al. "Diamond–like carbon from the ion–beam decomposition of polyphenyl ether," *Applications of Diamond Films & Related Materials*, (1991) 833–838. No Month.

J. A. Davidson, et al. "Surface Modification Issues for Orthopaedic Implant Bearing Surfaces," *Surface Modification Technologies*V, (1992) 1–14. No Month.

P. Bodo, et al, "Adhesion of evaporated titanium to polyethylene: Effects of ion bombardment pretreatment," *J. Vac. Sci. Technol.*, A2 (4) (Oct.–Dec. 1984) 1498–1502.

(List continued on next page.)

*Primary Examiner*—Marianne Padgett

[57] ABSTRACT

The present invention provides a method for coating a titanium based component with diamond-like carbon to reduce the thrombogeneticity of the component. In a preferred embodiment, the titanium based component is a heart valve.

According to the present invention, the component is placed in a vacuum chamber and heated to about 600° –650° C. (1112°–1202° F.). Thereafter, silicon is then deposited onto the component, and the component is simultaneously bombarded with a beam of energetic ions to form a metal-silicide bonding layer. The component then is cooled to at least about 100° C. (212° F.), preferably about 80° C. (176° F.), and a diamond-like carbon precursor is condensed onto the metal-silicide bonding layer. The precursor is simultaneously bombarded with a beam of energetic ions to form a coating of diamond-like carbon.

25 Claims, No Drawings

OTHER PUBLICATIONS

P. Gao, et al. "Surface treatment of ultra high molecular weight polyethlene to enhance adhesion and conductivity properties," *Polymer*, 33:19 (1992) 4075–4080. No Month.

A. C. Evans, et al. "Diamond–Like Carbon Applied to Bioengineering Materials," *Medical Device Technology*, (May 1991) 26–29.

C. M. Agrawal, et al. "The Effects of Diamond–Like Carbon Coatings on the Friction and Wear of Enhanced UHMPE–Metal Couples," 19th Annual Meeting of the Society for Biomaterials, (Apr. 28–May 2, 1993) 10.

L. S. Wielunski, et al. "Improvement of thermally formed nickel silicide by ion irradiation," *J. Vac. Sci. Technol.* 20(2), (Feb. 1992) 182–184.

A. M. Jones, et al. "Stress and Microstructure of Diamond–Like Carbon from Ion–Beam Decomposition of Hydrocarbon Precursors," 2nd Annual European Conference on Diamond, Diamond–like and Related Coatings, (Sep. 1991) 1–18.

Browne, Malcolm W., "Diamond Coating May be Future of Tool Manufacture," Article in San Antonio Express News (Apr. 1, 1996).

R. S. Butter et al., "Diamond–Like Carbon for Biomedical Applications," Applied Diamond Conference (Aug. 21–24, 1995), pp. 683, 688 and 690.

5,605,714

TREATMENTS TO REDUCE THROMBOGENETICITY IN HEART VALVES MADE FROM TITANIUM AND ITS ALLOYS

The present application is a continuation-in-part of copending application Ser. No. 08/220,234, filed Mar. 29, 1994.

FIELD OF THE INVENTION

The present invention relates to decreasing the thrombogeneticity of heart valves and other medical implants made from titanium end its alloys.

BACKGROUND OF THE INVENTION

Titanium has become a popular metal for the manufacture of human implants. The FDA considers titanium and many of its alloys ("titanium based materials") to be biocompatible. Titanium based materials also ere easily machined, are not overly brittle, and are durable enough for the manufacture of most medical implants.

Unfortunately, titanium based materials also tend to encourage thrombogenesis. This tendency is undesirable, particularly for implants used in the circulatory system. An example of a medical implant that is used in the circulatory system is a heart valve.

A method for reducing the thrombogeneticity of titanium and its alloys would be highly desirable.

SUMMARY OF THE INVENTION

The present invention provides a method for coating a titanium based component with amorphous diamond-like carbon to reduce the thrombogeneticity of the component. In a preferred embodiment, the titanium based component is a heart valve.

According to the present invention, the component is placed in a vacuum chamber and heated to about 600°–650° C. (1112°–1202° F.). Thereafter, silicon is deposited onto the component, and the component is simultaneously bombarded with a beam of energetic ions to form a metal-silicide bonding layer. The component then is cooled to at least below about 100° C. (212° F.), preferably about 80° C. (176° F.), and a diamond-like carbon precursor is condensed onto the metal-silicide bonding layer. The precursor is simultaneously bombarded with a beam of energetic ions, preferably nitrogen ions, to form a coating of diamond-like carbon.

DETAILED DESCRIPTION OF THE INVENTION

Amorphous carbon, or "diamond-like carbon" ("DLC"), is biocompatible coating material that is less thrombogenic than titanium. A primary concern about using DLC for medical implants is the strength of the bond that forms between the substrate and the DLC coating. The present invention provides a method for coating titanium based components, particularly components for use in the circulatory system, with a tightly adhered coat of DLC to reduce the thrombogeneticity of the component.

The present invention ensures strong adherence between the DLC and the surface of the titanium based component by forming a titanium-silicide interlayer. In order to knit the successive layers of metal-silicon-DLC together effectively, it is necessary to supply a bond-interface for the metal-silicon bond as well as for the silicon-DLC bond. Without limiting the present invention, it is believed that the present method achieves this result by forming strong interatomic bonds having a character that is intermediate to the type of bond that exists between the atoms in the metal and the type of bonds that exist in the silicon. Silicon is chosen as the substance to form the interlayer because (a) DLC is known to adhere better to silicon then to any other substrate—which is attributed to strong SiC bonds formed at the interface of the two materials—and (b) titanium is known to react with silicon to form a disilicide ($TiSi_2$) when reacted with silicon.

The method for coating the titanium based components uses ion beam assisted deposition of silicon, followed by deposition of DLC. After conventional cleaning of the component to remove superficial contaminants, such as grease, the component is placed in a vacuum chamber that has been evacuated to a base pressure or preferably less than about $10^{-5}$ torr. The component then is bombarded with ions, preferably argon ions, at an energy range between about 10–100 KeV, preferably around 10 keV. This ion bombardment provides an effective means to remove some of the remaining adsorbed atoms from the surface.

The component then is heated. Titanium based components tend to have a thin oxide layer on their surface which should be removed in order to form the silicide interlayer. This is accomplished by heating the titanium component sufficiently to "dissolve" the oxide layer. The component preferably should be heated to about 600°– 650° C. (1112°–1202° F.) before condensing silicon on the surface of the component.

After the component has been heated and while remaining at that temperature, silicon can be deposited on the surface of the component using known means. A preferred means is to position the workplace directly over a volatilization hearth which is maintained at a preferred temperature of about 1900° C. (3450° F.), until a preferred coating thickness of between about 100–200 nm has been achieved. The thickness of the coating may be monitored by standard methods, e.g., using the frequency change of a quartz crystal oscillator.

The component preferably should be simultaneously bombarded with an energetic beam of ions, preferably nitrogen ions, at an energy range between about 500 eV to 100 keV, preferably between about 10–20 key, in order to form a layer of titanium silicide at the titanium-silicon interface. Nitrogen is preferred for the ion beams of the present invention because nitrogen ions actually will bond with the substrate/coating or interlayer. Inert ions, such as argon and/or helium ions, will not bond with the substrate/film. The use of inert ions could result in bubbling and/or a weaker coating. Although it has not been proven, it is believed that strong carbon-nitrogen bonds form in the DLC layer when the ions used to make the DEC are nitrogen ions. In any event, the use of a beam of nitrogen ions can result in DLC coatings that increase wear resistance and decrease friction up to 5–7 times more than DLC coatings formed using other types of ions.

Although nitrogen ions are preferred, other ions maybe used, such as argon, hydrogen, silicon, methane, helium, or neon, having en energy between 500 eV to 100 keV, preferably 10–30 keV. The ion-to-atom ratio should be sufficient, preferably at least 1 ion to 10 silicon atoms, to form a layer of metal silicide at the metal-silicon interface.

Thereafter, the component should be cooled to at least below about 100° C. (212° F.), preferably to about 80° C. (176° F.). The cooling preferably should be done without removing the component from the vacuum chamber. Thereafter, a diamond-like carbon (DLC) precursor should be deposited. In a preferred embodiment, the DLC precursor is polyphenyl ether. Other suitable precursor materials include carbon-based diffusion pump materials which have a low vapor pressure and can be vaporized stably at room temperature. Preferable diffusion pump fluids include, but are not necessarily limited to: polyphenyl ether; polydimethyl siloxane; pentaphenyltrimethyl siloxane; and, elcosyl napthalene.

The precursor is vaporized and condensed onto the surface of the component using known means. Generally, the precursor is placed in a reservoir, heated to between about 150° C.–170° C. (302° F.–338° F.), and directed onto the cooled component. Substantially simultaneously, the component should be bombarded, either in a continuous or interrupted fashion, with an energetic beam of ions. A preferred ion source is nitrogen. Other suitable ions include, but are not necessarily limited to, argon, hydrogen, silicon, methane, helium, or neon. The ion beam should have an energy between about 500 eV to 100 keV, preferably between about 10–30 keV. The energy of bombardment must be sufficient to ionize the constituent molecules in the precursor film, and to rupture the bonds between hydrogen and other atoms, thereby releasing the hydrogen into the surrounding vacuum to be pumped away.

The rate of arrival of the ions should be controlled in relation to the rate of arrival of the precursor molecules. This process should require about one ion for every 100 atoms in the final product coating; however, the ion-to-atom ratio will vary according to the mass and energy of the ion species. Typically, 100 eV must be deposited for each carbon atom in the coating. Persons of ordinary skill in the art will recognize how to achieve the correct linear energy of transfer in the ionizing process. The procedure should be continued until a thickness of DLC between about 100 nm–10 microns is achieved.

EXAMPLE 1

A DLC coating of approximately 1 micron in thickness is prepared by nitrogen ion bombardment of a polyphenyl ether precursor. A titanium based heart valve comprised of a titanium alloy containing vanadium and aluminum is cleaned in isopropyl alcohol prior to coating. Isopropyl alcohol is chosen because it leaves few, if any, residues. Wear testing reveals that, under some circumstances, there could be a loss of adhesion of the coating.

EXAMPLE 2

A titanium alloy heart valve of the same composition as in Example 1 is treated using a bond-coat of silicon. After conventional solvent cleaning of the component to remove superficial contaminants, such as grease, the component is placed in a vaccuum chamber that has been evacuated to a base pressure of $10^{-5}$ torr. The component then is bombarded with nitrogen ions at an energy of about 10 keV to remove some of the remaining adsorbed atoms from the surface.

The component is heated to about 600° C. (1112° F.). Silicon then is deposited onto the outer surface of the component. The workplace is positioned directly over the volatilization hearth which is maintained at e temperature of about 1900° C. (3450° F.), until a preferred coating thickness of about 100 nm has been achieved. The thickness of the coating is monitored by standard methods, e.g., using the frequency change of a quartz crystal oscillator.

The component is simultaneously bombarded with an energetic beam of nitrogen ions at an energy of about 20 keV and an ion-to-atom ratio of at least 1 ion to 10 silicon atoms for about 15 minutes to form a layer of metal silicide at the metal-silicon interface.

Thereafter, the component is cooled to about 80° C. without removing the component from the vacuum chamber. Polyphenyl ether is heated to at least about 150° C. (302° F.) end condensed onto the surface of the component. The component simultaneously is bombarded with an energetic beam of nitrogen ions having an energy of about 20 key and an ion-to-atom ratio of at least 1 ion to 100 precursor molecules. The procedure is continued until a thickness of DLC of about 100 nm is achieved.

In prolonged wear tests, at a contact pressure of 6.9 MPa under serum, i.e., load and environmental conditions equivalent to those encountered in vivo by a heart valve, no decohesion or lose of DLC is observed after about 10.0 million reciprocated wear cycles.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A method for coating a substrate comprised of titanium with diamond-like carbon comprising:

exposing said substrate to a vacuum at a pressure of about $10^{-5}$ torr or less;

heating said substrate to between at least about 600° C.–650° C. (1112° F.–1202° F.);

depositing silicon onto said substrate in an amount sufficient to form an inner bonding layer of titanium-silicide cohesively bonded to an outer layer of silicon;

substantially simultaneous with said depositing of silicon, bombarding said deposited silicon with a first energetic beam of ions at a first energy, a first ion density, and for a first amount of time sufficient to form said inner titanium-silicide bonding layer cohesively bonded to said outer layer of silicon;

condensing a diamond-like carbon precursor onto said outer layer of silicon at a second temperature and for a second amount of time sufficient to form a film of precursor molecules tin said outer layer of silicon, wherein said second temperature is sufficiently low that said diamond-like carbon precursor is not vaporized off of said substrate;

substantially simultaneous with said condensing of a diamond-like carbon precursor, bombarding said diamond-like carbon precursor with a second energetic beam of ions at a second energy, a second ion density, and for a third amount of time sufficient to form an inner silicon carbide layer cohesively bonded to an outer coating of diamond-like carbon.

2. The method of claim 1 wherein said first and second beam of ions comprise ions selected from the group consisting of nitrogen, argon, hydrogen, silicon, methane, helium, neon, and combinations thereof.

3. The method of claim 1 wherein said second beam of ions comprises nitrogen ions.

4. The method of claim 1 wherein said first energy and said second energy are between about 10–30 keV.

5. The method of claim 2 wherein said first energy and said second energy are between about 10–30 keV.

6. The method of claim 3 wherein said first energy and said second energy are between about 10–30 keV.

7. The method of claim 1 wherein said second temperature is less than or equal to about 100° C. (212° F.).

8. The method of claim 2 wherein said second temperature is less than or equal to about 100° C. (212° F.).

9. The method of claim 3 wherein said second temperature is less than or equal to about 100° C. (212° F.).

10. The method of claim 4 wherein said second temperature is less than or equal to about 100° C. (212° F.).

11. The method of claim 6 wherein said second temperature is less than or equal to about 100° C. (212° F.).

12. The method of claim 1 wherein said silicon is deposited onto said substrate to a thickness of between about 100–200 nm.

13. The method of claim 2 wherein said silicon is deposited onto said substrate to a thickness of between about 100–200 nm.

14. The method of claim 3 wherein said silicon is deposited onto said substrate to a thickness of between about 100–200 nm.

15. A medical implant having at least one substrate comprising titanium coated with a sequential gradient as follows:

silicon chemically bonded to said titanium, forming a first layer comprising titanium-silicide;

silicon cohesively bonded to said titanium-silicide, forming a second layer comprising silicon;

carbon chemically bonded to said silicon, forming a third layer comprising silicon carbide; and carbon cohesively bonded to said silicon carbide, forming a fourth layer comprising diamond-like carbon.

16. The medical implant of claim 15 wherein said diamond like carbon has a thickness of at least about 1µ.

17. The medical implant of claim 16 further comprising nitrogen ions bonded to said carbon in said diamond-like carbon.

18. The medical implant of claim 15 further comprising nitrogen ions bonded to said carbon in said diamond-like carbon.

19. A solid substrate comprising titanium coated with diamond-like carbon by a process comprising:

exposing said substrate to a vacuum at a pressure of about $10^{-5}$ torr or less;

heating said substrate to between at least about 600° C.–650° C. (1112° F.–1202° F.);

depositing silicon onto said substrate in an amount sufficient to form an inner bonding layer of titanium-silicide cohesively bonded to an outer layer of silicon;

substantially simultaneous with said depositing of silicon, bombarding said deposited silicon with a first energetic beam of ions at a first energy, a first ion density, and for a first amount of time sufficient to form said inner titanium-silicide bonding layer cohesively bonded to said outer layer of silicon;

condensing a diamond-like carbon precursor onto said outer layer of silicon at a second temperature and for a second amount of time sufficient to form a film of precursor molecules on said outer layer of silicon, wherein said second temperature is sufficiently low that said diamond-like carbon precursor is not vaporized off of said substrate;

substantially simultaneous with said condensing of a diamond-like carbon precursor, bombarding said diamond-like carbon precursor with a second energetic beam of ions at a second energy, a second ion density, and for a third amount of time sufficient to form an inner silicon carbide layer cohesively bonded to an outer coating of diamond-like carbon.

20. The substrate of claim 19 wherein said diamond-like carbon coating has a thickness of at least about 1µ.

21. The substrate of claim 19 wherein said second beam of ions comprises nitrogen ions.

22. The substrate of claim 20 wherein said second beam of ions comprises nitrogen ions.

23. The substrate of claim 19 wherein said silicon is deposited onto said substrate to a thickness of between about 100–200 nm.

24. The substrate of claim 20 wherein said silicon is deposited onto said substrate to a thickness of between about 100–200 nm.

25. The substrate of claim 22 wherein said silicon is deposited onto said substrate to a thickness of between about 100–200 nm.

* * * * *